United States Patent
Hutchinson et al.

(10) Patent No.: US 6,532,803 B2
(45) Date of Patent: *Mar. 18, 2003

(54) SOIL MOISTURE DETECTION

(75) Inventors: Paul Andrew Hutchinson, Holder (AU); Richard Stirzaker, Cook (AU)

(73) Assignee: Commonwealth Scientific and Industrial Research Organisation, Campbell (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/384,920

(22) Filed: Aug. 27, 1999

(65) Prior Publication Data

US 2002/0066305 A1 Jun. 6, 2002

Related U.S. Application Data

(63) Continuation of application No. PCT/AU98/00128, filed on Feb. 24, 1998.

(30) Foreign Application Priority Data

Feb. 28, 1997 (AU) ............................................. PO5408
Oct. 13, 1997 (AU) ............................................. PO9775

(51) Int. Cl.$^7$ .......................... G01N 05/02; G01N 25/56
(52) U.S. Cl. ........................................................ 73/73
(58) Field of Search .............................................. 73/73

(56) References Cited

U.S. PATENT DOCUMENTS

| | | | | |
|---|---|---|---|---|
| 2,776,860 A | * | 1/1957 | Griffis ........................... | 299/25 |
| 3,297,254 A | * | 1/1967 | Coffman ...................... | 239/63 |
| 3,823,874 A | * | 7/1974 | Kroeck ........................ | 239/65 |

(List continued on next page.)

FOREIGN PATENT DOCUMENTS

| | | |
|---|---|---|
| AU | 2418623 | 11/1979 |
| AU | 33245 | 9/1984 |
| AU | 9306709 | 4/1993 |
| AU | 15097 | 9/1997 |
| EP | 0305614 | * 3/1989 |
| FR | 9120004 | 12/1991 |
| GB | 883184 | 11/1961 |
| GB | 9203916 | 3/1992 |
| SE | 8705116 | 8/1997 |

OTHER PUBLICATIONS

Supplementary European Search Report in connection with European Application No. EP 98905147.

Magid J. and Christensen N., "Soil Solution Sampled With And Without Tension In Arable And Heathland Soils", (1993), Soil Sci. Soc. Am. J. 57: 1463–1469.

Philip, JR Knight and RT Waechter., "Unsaturated Seepage And Subterranean Holes: Conspectus, and Exclusion Problem For Circular Cylindrical Cavities", (1989), Water Resources Research., 25: 16–28.

Jordan, CF, "A Simple, Tension–Free Lysimeter", (1968), Soil Sci., 105: 81–86.

Liator, MI, "Review Of Soil Sampling Samplers", (1998), Water Resources Research, 24: 727–733.

Primary Examiner—Hezron Williams
Assistant Examiner—Michael Cygan
(74) Attorney, Agent, or Firm—John P. White; Cooper & Dunham LLP

(57) ABSTRACT

A detection assembly for detecting moisture within an unsaturated permeable soil or soil-like medium is disclosed which includes a funnel 11 having a surface inclined in use to the vertical for distorting the flow streamlines within the medium to cause an increase in fluid content and saturation at points in the permeable medium; a cup 13 beneath the funnel for collecting free fluid from the saturated permeable medium; a sensor 14 for detecting the presence of free fluid formed upon saturation within the permeable medium, and a vent 16 for venting air from said collection means.

11 Claims, 2 Drawing Sheets

U.S. PATENT DOCUMENTS

| | | | | |
|---|---|---|---|---|
| 3,872,179 A | * | 3/1975 | Andersen et al. | 208/121 |
| 3,908,385 A | * | 9/1975 | Daniel et al. | 405/37 |
| 4,153,881 A | * | 5/1979 | Permut et al. | 340/620 X |
| 4,396,149 A | | 8/1983 | Hirsch | |
| 4,541,446 A | * | 9/1985 | Hogan | 73/304 R |
| 4,718,446 A | * | 1/1988 | Simpson | 137/624.11 |
| 4,947,888 A | * | 8/1990 | Tanner | 340/620 X |
| 4,952,868 A | * | 8/1990 | Scherer, III | 137/78.3 |
| 5,060,859 A | * | 10/1991 | Bancroft | 137/78.3 |
| 5,179,347 A | * | 1/1993 | Hawkins | 324/694 |
| 5,337,777 A | | 8/1994 | Shaw et al. | |
| 5,419,655 A | * | 5/1995 | Phillips et al. | 405/129.57 |
| 5,546,974 A | * | 8/1996 | Bireley | 137/624.12 |
| 5,644,947 A | * | 7/1997 | Hubbell et al. | 73/152.54 |
| 5,677,499 A | * | 10/1997 | Sullivan et al. | 73/863.23 |

* cited by examiner

SOIL MOISTURE DETECTION

This application is a continuation of PCT International Application No. PCT/AU98/00128, filed Feb. 24, 1998, designating the United States of America, which is claiming priority of Australian Application No. PO 5408, filed Feb. 28, 1997 and Australian Application No. PO 9775, filed Oct. 13, 1997, the contents of which are hereby incorporated by reference into the present application.

TECHNICAL FIELD

This invention relates to moisture detection.

As used herein the expression "moisture" is to be given a broad meaning and refers to fluids, particularly water, in a porous medium and/or the solutes contained therein.

The invention has particular but not exclusive application to agricultural methods and apparatus for detecting when adequate irrigation has been applied to the soil and for illustrative purposes reference will be made to such application. However it will be appreciated that the invention may be utilised in other applications which involve the detection of moisture.

BACKGROUND OF INVENTION

Devices which can assist irrigators to apply water in accordance with plant requirements are known. These include sensors based on electric, thermal and matric suction measurements (gypsum blocks, thermal probes, capacitance probes and tensiometry), and dielectric or radiation absorption measurements (time domain reflectometry, neutron scattering). These sensors vary in their cost, robustness, accuracy and the complexity of operation.

SUMMARY OF INVENTION

The present invention aims to provide an alternative to known methods and apparatus for moisture detection.

This invention in one aspect resides broadly in a method of detecting moisture within an unsaturated permeable medium, the method including:
  distorting the flow streamlines within the unsaturated permeable medium to increase the fluid content at points therein, and
  detecting the increased fluid content.

In another aspect this invention resides broadly in a detection assembly for detecting moisture within an unsaturated permeable medium, the assembly including:
  streamline distortion means for distorting the flow streamlines within the medium to increase the fluid content at points therein, and
  detection means for detecting the increased fluid content.

As used herein the expression "flow streamline" refers to the trajectory followed by a fluid particle moving through a permeable medium.

In a preferred embodiment the detection means constitutes switching means for activating a circuit to generate a signal. The configuration of the streamline distortion means may be such that operation of the switching means within a predetermined time indicates a given moisture content within the unsaturated permeable medium.

It is preferred that the flow streamlines are distorted to cause saturation at points in the permeable medium and that the detection assembly includes collecting means for collecting free fluid from the saturated permeable medium.

As used herein the expression "free fluid" means fluid which has a free boundary and which is able to be poured.

In a preferred embodiment the streamline distortion means includes a surface inclined to the flow streamlines within the permeable medium.

The streamline distortion means may thus have a variety of shapes and configurations and could for example be a planar surface, a sphere or a cylinder. In a preferred embodiment the streamline distortion means is a funnel and the collecting means includes a chamber located proximate the outlet of the funnel. Preferably the assembly includes vent means for venting the chamber, and suction means for generating a suction within the chamber.

In another aspect this invention resides broadly in an irrigation control assembly including:
  a funnel;
  a moisture detector located proximate the outlet of the funnel,
  and indicating means for providing an indication that a given moisture content has been detected by the moisture detector.

The indicating means may generate an alarm or alternatively the indicating means may generate a signal to stop irrigation.

In a further aspect this invention resides broadly in a method of controlling irrigation, the method including:
  locating a funnel in a medium to be irrigated;
  detecting the presence of a given irrigating fluid content in the medium within the funnel or proximate the outlet thereof, and
  ceasing the irrigation upon detection of the given irrigating fluid content.

In yet another aspect this invention resides broadly in a method of irrigating a crop planted in a planting medium, the method including:
  locating streamline distortion means in the planting medium within or proximate the crop plant root zone, the streamline distortion means having a surface inclined to the flow streamlines in the planting medium;
  detecting the presence of free irrigating fluid formed by the streamline distortion means;
  generating a signal upon detecting the presence of the free irrigating fluid, and
  ceasing irrigation in response to generation of the signal.

This invention also resides broadly in a method of nutrient scheduling and/or pollution monitoring within a permeable medium, the method including:
  locating streamline distortion means in the medium, the streamline distortion means having a surface inclined to the flow streamlines in the medium;
  detecting the presence of fluid formed by the streamline distortion means;
  collecting the fluid, and
  analysing the collected fluid.

This invention also resides broadly in a method of assessing drainage below the crop plant root zone of a crop planted in a planting medium, the method including:
  locating streamline distortion means in the planting medium within or proximate the crop plant root zone, the streamline distortion means having a surface inclined to the flow streamlines in the planting medium;
  detecting the presence of fluid formed by the streamline distortion means, and
  measuring the time elapsed between initial detection of the presence of the fluid and cessation of detection of the presence of the fluid.

This invention also resides broadly in a method of controlling the rotation of crops planted in a planting medium, the method including:

locating streamline distortion means in the planting medium within and below the crop plant root zone, the streamline distortion means having a surface inclined to the flow streamlines in the planting medium;

detecting the presence of fluid formed by the streamline distortion means;

measuring the depth to which the fluid has penetrated, and rotating the crops in accordance with the depth.

This invention also resides broadly in a method of delaying irrigation in accordance with rainfall, the method including:

locating a funnel in a medium to be irrigated;

detecting the presence of rainfall in the medium within the funnel or proximate the outlet thereof, and controlling the irrigation in accordance with detection of rainfall.

In another aspect this invention resides broadly in a detection assembly for detecting moisture within an unsaturated permeable medium, the assembly including:

streamline distortion means for distorting the flow streamlines within the medium to increase the fluid content at points therein;

detection means for detecting the increased fluid content;

collecting means for collecting free fluid from the saturated permeable medium, and vent means for venting the collecting means to a space within the detection assembly.

In a preferred embodiment the space is between the collecting means and a detection assembly housing.

DESCRIPTION OF DRAWINGS

In order that this invention may be more easily understood and put into practical effect, reference will now be made to the accompanying drawings which illustrate a preferred embodiment of the invention, wherein.

DESCRIPTION OF PREFERRED EMBODIMENT OF INVENTION

In general terms, in a preferred embodiment the irrigation sensor of the present invention has a funnel-shaped container at the base of which is fixed a sensor having a conductivity cell. In a preferred form of the invention the container is a plastic funnel and a sintered glass cylinder is fixed within a brass cup at the base of the cone. The conductivity cell comprises a conductive brass cup and a conductive long brass pin, each of which is electrically isolated from the other. The pin is mounted on the inside of the sintered glass cylinder. These two conductors are electrically connected to an alternating current source which in the preferred embodiment may be a fluid detector such as the LM1830 manufactured by National Semiconductor.

Figure 1:
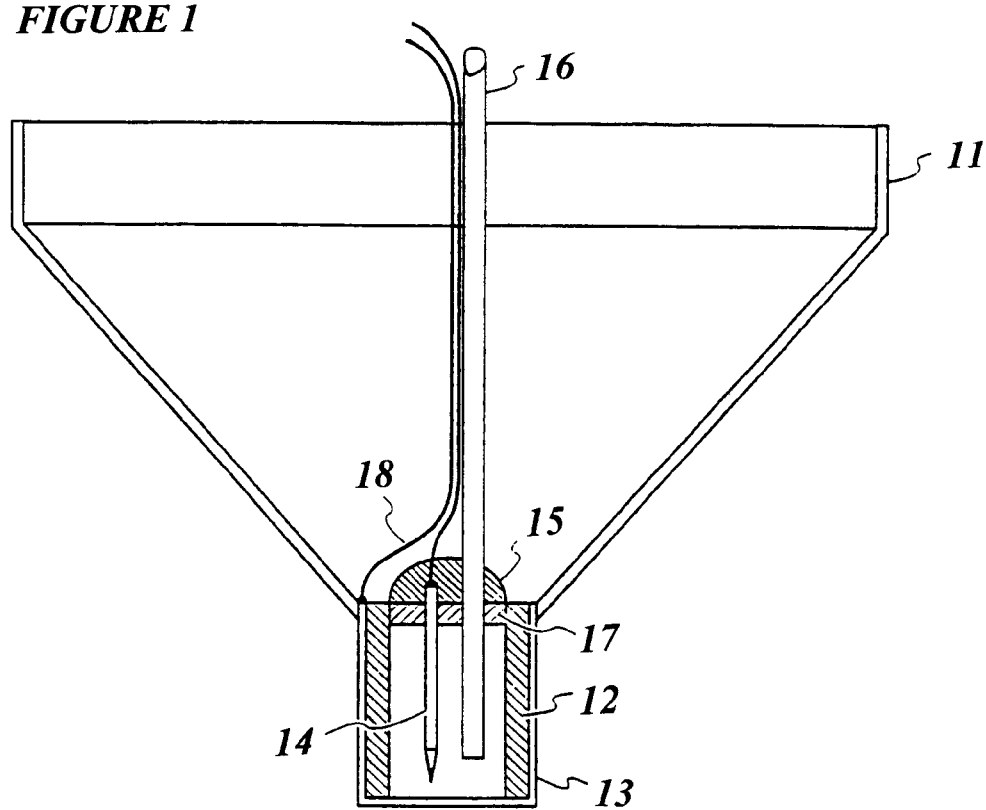
FIGS. 1 and 2 illustrate preferred embodiments of an irrigation scheduling sensor according to this invention.

More specifically as illustrated in FIG. 1, brass cup 13 is located at the base of funnel-shaped container 11. Sintered glass cylinder 12 is located within brass cup 13. Rubber cap 17 plugs the upper end of the sintered glass cylinder 12 and has holes drilled to accept brass pin 14 and vent tube 16. Electrical wires 18 are connected to brass cup 13 and brass pin 14. A waterproof sealant 15 is applied to rubber cap 17 to electrically isolate brass pin 14 and its electrical connection from the soil. Vent tube 16 extends to the soil surface.

Figure 2:
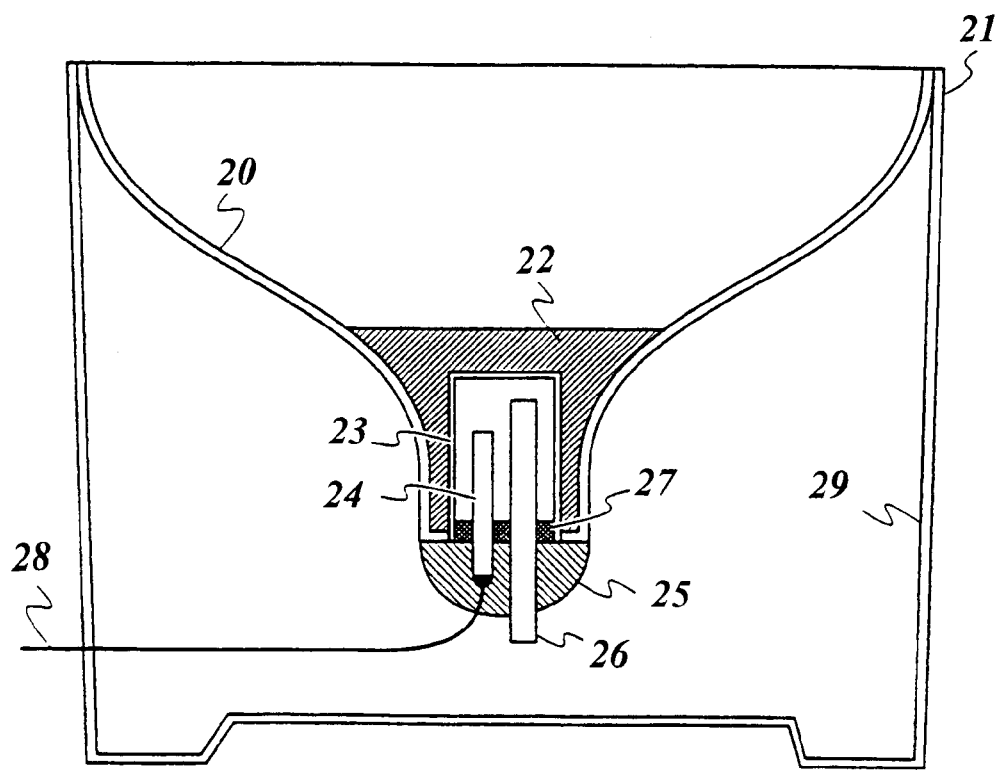

In another form of the invention illustrated in FIG. 2, irrigation sensor 21 has a substantially wine-glass shaped container 20 to optimise the convergence of the flow into the container and minimise the loss due to capillarity.

An apertured cylinder 23 is located in the base of wine-glass funnel 20 and sealed therein by a rubber cap 27 which plugs the lower end of the funnel. Plug 27 has holes drilled to accept brass pine 24 (which are illustrated in alignment in FIG. 2 such that only one is visible) and vent tube 26. Electrical wires 28 are connected to brass pins 24. A porous medium 22 encapsulates cylinder 23 at the lower end of funnel 20. A waterproof sealant 25 is applied to rubber cap 27 across the base of funnel 20 to electrically isolate brass pins 24 and its electrical connection from moisture. Vent tube 26 extends into the space between funnel 20 and casing 29 which houses the assembly.

As opposed to the arrangement in FIG. 1 where the conductivity cell is vented to ground level, vent 26 vents conductivity cell 23 to the air space between funnel 20 and outer casing 29. Consequently no part of the assembly protrudes to the surface thus avoiding mowing problems associated with the FIG. 1 embodiment if located in a lawn.

The containers may have a range of sizes to suit different soil types.

If the background potential energy produced during irrigation is approximately the same as the minimum potential energy required to produce saturation in the porous cup, then the sensor can take an unacceptably long time to trigger. To overcome this limitation, one form of the invention may contain suction means to produce a suction within the porous cup. The suction may be periodically or continuously applied.

In use the sensor is placed towards the bottom of the plant root zone, and activates an alarm or a solenoid valve when the irrigation water has percolated to the required depth. The container is filled with soil and buried with the funnel opening upper-most and within or below the root zone of the crop.

Upon irrigating, a portion of the unsaturated flow converges into the bottom of the container causing the water content there to increase. Provided the irrigation rate is sufficient to produce a background potential energy above some minimum value, the soil at the base of the funnel reaches saturation and the water seeps through the porous cylinder to partially fill the conductivity cell. The air displaced as the water enters the conductivity cell passes to the surface through the vent tube in the case of the embodiment of FIG. 1, or to the space between the funnel and its casing in the embodiment of FIG. 2.

The cell is activated immediately water is present in the cup and an alarm or water solenoid is activated to turn the irrigation off. Over a period of some hours as the soil dries, the water in the cell is withdrawn back into the soil by capillary suction and the sensor is reset ready for a future irrigation event.

The output signal from the fluid detector may be connected to a microprocessor controlling the irrigation schedule or may be operated in isolation whereby the irrigator responds to an alarm by turning off the irrigation.

Whilst the operational principles underlying the broad aspects of the invention will be readily apparent, a more detailed explanation will now be given of the some theoretical and operational aspects of the two preferred embodiments of the inventions illustrated in FIGS. 1 and 2. However these are not to be construed as limiting on the invention per se.

As indicated above the containers may have a range of sizes to suit different soil types. Having regard to the embodiments of FIGS. 1 and 2, two parameters which determine performance are the maximum size of the container and its depth. In these embodiments it is also to be noted that the sides of the container converge to a relatively small area and that the container is upwardly concave thereby converging the flow to the bottom of the container. To facilitate this the sides of the container are inclined to the flow streamlines some distance away from the moisture detector.

A theoretical explanation of the operational characteristics of the moisture detectors in the illustrated preferred embodiments can be given by reference to the potential energies which occur Moist soil is said to have negative potential energy because energy is required to extract the water tightly held by the soil particles. This energy can be measured as a suction in centimetres or millimetres of water. Thus a glass of water 5 cm deep is said to have a potential energy of +5 cm ie a positive energy equivalent to the depth of water. Soil which is saturated has an energy of 0 cm. Soil which is moist has a negative value.

As described above the detector trips when there is free water in the conductivity cell. If this tripping is operable to cease irrigation activities, the suction in the soil surrounding the moisture detector, ie background negative potential energy will be typical of values found above the wetting front during irrigation. There is thus a minimum background potential energy where the detector must trip.

The minimum background potential energy required to produce saturation is dependent on container size and slightly dependant on soil type and container shape. It is determined by the process of streamline convergence about a buried object caused by the interaction of gravity and capillarity.

An object inserted in a permeable medium will cause flow streamlines to distort. If the object has an upwards configuration, the streamlines will be distorted within the object and will converge. Where streamlines converge the fluid content is increased. The larger a specific object, the larger will be the increase in fluid content.

Soil can transport moisture in any direction through capillary suction provided there are no impermeable barriers in the way, the moisture at any point moving at a rate depending on the spatial gradient in moisture content and the physical properties of the soil. If the spatial gradient is decreased by inserting a partial barrier between the moist and dry soil, transport due to capillarity will be decreased. Increasing the depth of the container decreases the transport of fluid by capillarity because the sides of the container are a partial barrier to flow.

The dimensions of the containers in the illustrated preferred embodiments of the invention were chosen so that the increase in fluid content due to flow streamline convergence such that at the base of the container the fluid content is increased to the point of saturation.

The moisture detectors of the preferred illustrated embodiments may be considered to potentiometers which "tripe" at a particular energy potential.

As one example, in the irrigation of standard agricultural soils with standard irrigation equipment, it is desirable that the minimum background negative potential energy must be leas than approximately −10 cm. This is achieved in the preferred embodiments illustrated by a container having a funnel diameter of approximately 20 cm and a funnel depth of approximately 10 cm.

In summary, the minimum background potential energy required to produce saturation is dependent on container size and slightly dependent on soil type and container shape. Except for very small containers it is generally less than the background potential energy obtained when a soil is irrigated with standard sprinkler or micro-irrigation technologies.

The embodiments described above with reference to the drawings suggests chat the funnel is to be filled with the soil displaced when digging the hole to install the sensor. Alternatively, the funnel can be filled with other porous material which can change the response time of the detection assembly. In particular, the funnel can be filled with material of high conductivity and low water holding capacity to shorten the response time for shallow rooted crops.

Figure 3:
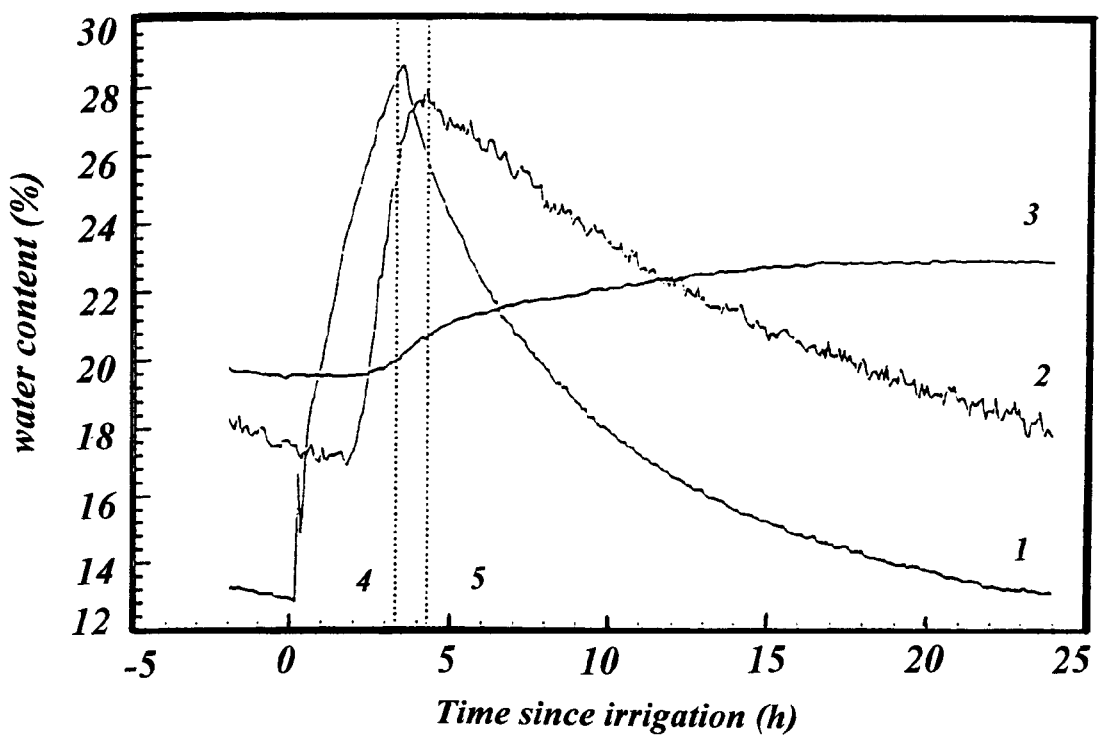
FIG. 3 illustrates the result of a laboratory experiment where the sensor of FIG. 1 was buried at a depth of 50 cm in a fine sand and results compared with measurements made with Time Domain Reflectometry (TDR)

FIG. 3 illustrates evolution of water content within a fine sand in a laboratory tank. The horizontal axis denotes time elapsed since the commencement of irrigation. The detector was buried at a depth of 50 cm and the water content determined using TDR. Irrigation was applied with a disk permeammeter at the rate of 8.4 litre per hour. Plot 1 is the water content measured near the base of the funnel, plot 2 is the average water content in the layer between the surface and 45 cm depth, and plot 3 is the average water content in the zone between 55 and 125 cm depth. Dotted line 4 indicates the time when water was detected within the conductivity cell and when the irrigation was halted. Line 5 indicates the time when the last of the water in the conductivity cell was drawn back into the soil and the sensor reset.

Figure 4:
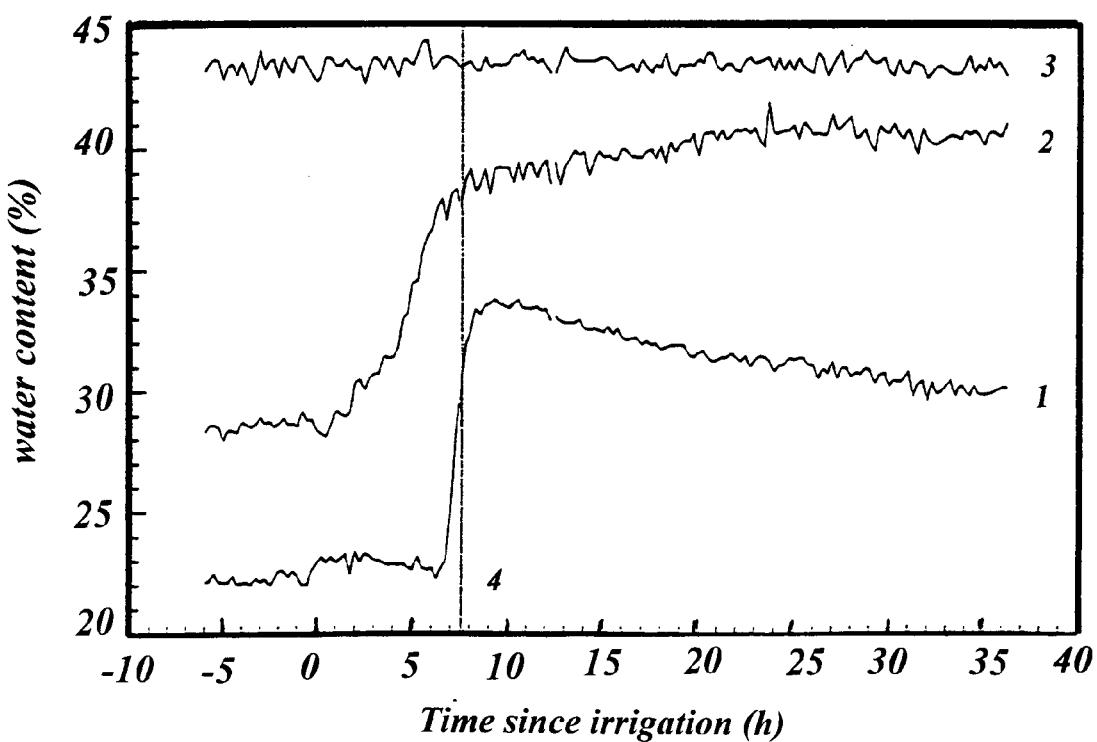
FIG. 4 illustrates the result of an experiment where the sensor of FIG. 1 was buried within a lucerne crop and results compared with measurements made with TDR.

FIG. 4 illustrates evolution of water content within a bed of lucerne grown in a clay soil. The abscissa axis denotes time elapsed since the commencement of irrigation. The detector was buried with the sensor at a depth of 57 cm and the water content determined using TDR. Irrigation was applied with an overhead micro-jet at the rate of 9.5 mm per hour. Plot 1 is the water content measured near the base of the funnel, plot 2 is the average water content in the layer between the surface and 60 cm depth and plot 3 is the average water content in the zone between 60 and 90 cm depth. Line 4 indicates the time when water was detected within the conductivity cell and when the irrigation was halted. Over a 24 hour period after irrigation a negligible amount of water was applied to the soil below the sensor because the water applied to the surface (71 mm) was retained in the 0–60 cm layer and there is no change in the average water content in the 60–90 cm layer (plot 3).

Referring to plot 2, as the average water content in the 0–60 cm layer before irrigation was 28.5% and 24 hours after irrigation the average water content was 41%, the water added to the 0–60 cm layer was approximately 75 mm, ie (41%−28.5%)=12.5% of 600 mm. The water content within the irrigation sensor (plot 1) was rapidly changing at the time when water was detected in the conductivity cell and soon after irrigation was halted the water content inside the sensor decreased.

Other preferred embodiments and applications of the invention include (a) nutrient scheduling/pollution monitoring, (b) drainage and crop rotation and (c) rain sensing and irrigation control. These are separately described in greater detail as follows:

(a) Nutrient Scheduling/Pollution Monitoring

For the sensor of the detection assembly to "trip", a small amount of water must collect in the conductivity cell at the base of the funnel. In a preferred embodiment this water is extracted via the vent tube and analysed for soluble nutrients such as nitrate. Sensors can be placed at the bottom of the root zone to monitor the movement of agricultural pollutants such as salt or pesticides to rivers or ground water bodies.

The water sample can be collected manually shortly after the sensor trips, or collection can be automated by connecting the vent tube to a suction tube and opening a solenoid valve in response to water being detected in the cell.

This method is an improvement over known methods of sampling utilising ceramic suction caps connected to a suction tube or taking soil samples, diluting with water and filtering.

(b) Drainage and Crop Rotation

The amount of water moving below the root zone of crops is extremely difficult to measure even with sophisticated equipment. A useful approximation of drainage is the time that a layer of soil has been at or near saturation. The length of time the sensor detects water in the conductivity cell provides this information.

This has application for irrigators and dryland farmers. For example grain farmers can use this application for deciding when to change from a shallow rooted cereal crop to a deep rooted pasture crop once a certain amount of water had reached the deep sub soil.

(c) Rain Sensing and Irrigation Control

Most irrigation controllers apply water at a predetermined time interval. This time interval must be adjusted if rain falls before a scheduled irrigation event. If sufficient rain falls so that the detection assembly detects water, the irrigation interval can be postponed. This prevents over irrigation, or irrigation during rainfall.

It will be appreciated that the present invention bar a number of advantages over known systems and methods of moisture detection.

The application of water in excess of plant requirements is a serious problem worldwide. Excess irrigation is wasteful of a dwindling resource and can contribute to groundwater pollution when water draining below plant roots transports agrochemicals or mobilises salt. Excess irrigation frequently occurs because the cost and/or complexity of measuring soil water to facilitate informed irrigation decisions and irrigation control is often beyond the resources or ability of a majority of water users.

The cost and complexity arises because it is difficult to make accurate in-situ measurements of soil moisture content. The present invention overcomes the difficulty of measuring moisture content in an unsaturated state by forcing the soil to become saturated at a given location.

The sensor output is only activated when sufficient irrigation water has been supplied. Thus it is not necessary for the output to be interpreted or analysed as is necessary with the output from devices which measure partial rather than complete saturation.

Moreover because detection of saturation is technically trivial, the sensor of the present invention is relatively inexpensive to manufacture and is robust and durable.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

What is claimed is:

1. A method of detecting the arrival of moisture at a location within, or below the root zone of a plant growing in, an unsaturated permeable soil or soil-like medium, said method including:

positioning at said location streamline distortion means having a surface which in use is non-vertical for distorting the flow streamlines of fluid particles moving through unsaturated soil at said location to cause an increase in fluid content and to cause saturation at said location whereby free fluid is formed thereat;

collecting said free fluid in collecting means beneath said surface, a strainer means separating a permeable medium in the streamline distortion means from the collecting means and allowing free fluid to move from the permeable medium to or from the collecting means depending on the wetness of the permeable medium, the collecting means including an air filled cavity separated from the soil by the strainer or the like such that the collecting means and the permeable medium remain hydraulically connected, whereupon collection of free fluid in the collecting means air is vented therefrom via a substantially rectilinear conduit extending substantially vertically upwards from said collecting means to soil surface;

detecting the presence of the free fluid collected in the collecting means, the detection of the presence of the free fluid thereby indicating the arrival of moisture at said location; and signaling the presence of the free fluid to a location above the permeable medium to indicate the arrival of moisture at said location.

2. A method of detecting the arrival of moisture as claimed in claim 1, and including providing a signal to above the permeable medium to indicate that rain or irrigation water has reached said location.

3. A method of detecting the arrival of moisture as claimed in claim 1, wherein said surface is upwardly concave.

4. A method of detecting the arrival of moisture as claimed in claim 1, wherein the free fluid formed upon saturation within the permeable medium is collected in collection means at the base of the non-vertical surface.

5. A method of detecting the arrival of moisture as claimed in claim 4, wherein the presence of free fluid is detected by sensor means positioned in the collection means.

6. A detection assembly for detecting the arrival of moisture at a location within, or below the root zone of a plant growing in, an unsaturated permeable soil or soil-like medium, said assembly including:

streamline distortion means having a surface which in use is non-vertical for distorting the flow streamlines of fluid particles moving through unsaturated soil at said location to cause an increase in fluid content and to cause saturation at said location whereby free fluid is formed thereat;

collecting means beneath said surface for collecting said free fluid;

a substantially rectilinear conduit extending substantially vertically upwards from said collecting means to soil surface for venting air from said collecting means upon the collection of free fluid therein;

a strainer means separating a permeable medium in the streamline distortion means from the collecting means and allowing free fluid to move from the permeable medium to or from the collecting means depending on the wetness of the permeable medium;

detection means for detecting the presence of the free fluid collected in the collecting means, the detection of the presence of the free fluid thereby indicating the arrival of moisture at said location; and signalling means for signalling the presence of the free fluid to a location above the permeable medium to indicate that rain or irrigation water has reached said depth, said collecting means including an air filled cavity separated from the soil by said strainer means such that hydraulic continuity is maintained between the air filled cavity and the permeable medium.

7. A detection assembly as claimed in claim 6, wherein said surface is upwardly concave.

8. A detection assembly as claimed in claim 7, wherein said surface is a funnel.

9. A detection assembly as claimed in claim 8, wherein said collecting means includes an air filled cavity.

10. A detection assembly as claimed in claim 8, and including a housing supporting said funnel and forming a space therebetween, wherein said vent means vents said air filled cavity to said space.

11. A detection assembly as claimed in claim 6, wherein said detection means includes sensor means positioned in the collection means.

* * * * *